United States Patent [19]

Kvorning et al.

[11] Patent Number: 5,037,382
[45] Date of Patent: Aug. 6, 1991

[54] DISPOSABLE SYRINGE

[75] Inventors: Ingelise Kvorning, Olstykke; Anne Sorensen, Holte; Flemming Manique, Ballerup, all of Denmark

[73] Assignee: Novo Industri A/S, Denmark

[21] Appl. No.: 301,178

[22] Filed: Jan. 24, 1989

[30] Foreign Application Priority Data

Jan. 26, 1988 [DK] Denmark .................. 0340/88

[51] Int. Cl.⁵ ............................................. A61M 5/315
[52] U.S. Cl. ................................. 604/220; 604/187; 604/218
[58] Field of Search ............. 604/220, 110, 230, 218, 604/187, 199

[56] References Cited

U.S. PATENT DOCUMENTS

| Re. 28,713 | 2/1976 | Stevens et al. | 604/240 |
|---|---|---|---|
| 1,381,774 | 6/1921 | Weiner | 604/230 |
| 1,450,016 | 3/1923 | Bruce | 604/230 |
| 1,737,844 | 12/1929 | Heineman et al. | 604/230 |
| 3,667,657 | 6/1972 | Chiquiar-Arias | 604/110 |
| 4,074,715 | 2/1978 | Geiger | 604/230 |
| 4,500,310 | 2/1985 | Christinger | 604/228 |
| 4,820,272 | 4/1989 | Palmer | 604/110 |
| 4,888,002 | 12/1989 | Braginetz et al. | 604/220 |
| 4,932,941 | 6/1990 | Min et al. | 604/110 |

FOREIGN PATENT DOCUMENTS

| 374866 | 10/1921 | Fed. Rep. of Germany . |
| 7935103 | 12/1979 | Fed. Rep. of Germany . |
| 8014657 | 5/1980 | Fed. Rep. of Germany . |
| 52889 | 4/1979 | Japan .................... 604/230 |
| 1150980 | 5/1969 | United Kingdom ....... 604/110 |

OTHER PUBLICATIONS

South African Abstract for Application 73/3833–Jun. 6, 1973.

Primary Examiner—C. Fred Rosenbaum
Assistant Examiner—Mark O. Polutta
Attorney, Agent, or Firm—Willian Brinks Olds Hofer Gilson & Lione

[57] ABSTRACT

The present invention relates to a disposable syringe the barrel (4) of which is provided with a blob (6) of a cured adhesive substance on the barrel that prevents the piston (5) from being pulled out of the open rear end (8) of the barrel (4), for example when operated by an unexperienced person.

13 Claims, 1 Drawing Sheet

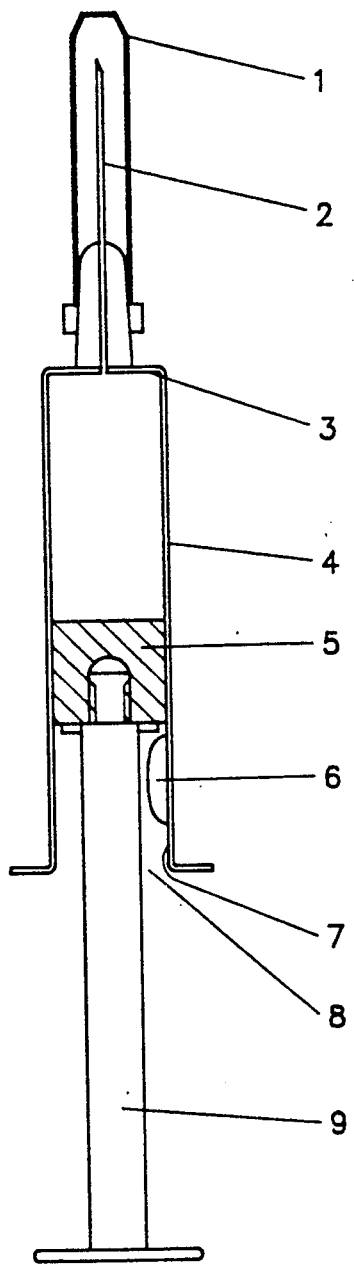

DISPOSABLE SYRINGE

BACKGROUND OF THE INVENTION

The present invention relates to a disposable hypodermic syringe comprising a barrel the front end of which is equipped with a firmly connected hypodermic needle or with a gland for fixing a hypodermic needle, in which barrel a tightly fitting piston can be displaced by means of a piston rod.

Various kinds of disposable syringes are known. Most frequently used are disposable syringes having a barrel made of a thermoplastic material. However, in some instances disposable syringes having a barrel made of glass are preferred in spite of the higher price. For both types of barrels the piston can be made of a suitable type of elastomer and the piston can be equipped with a piston rod made of a thermoplastic material. Alternatively the piston and the piston rod can be made in one piece of a suitable thermoplastic material possibly to be equipped with a gasket made of a suitable elastomer. A common feature with these disposable syringes is that the piston may slip out of the barrel during the filling of the syringe so that the contents will be spilled or the sterility spoiled or both if the piston rod is pulled too strongly.

Some barrels made of thermoplastic materials do have a circumferential bead on the inside of the rear part of the barrel in order to reduce the risk that the piston may slip out. However, since the bead is an integral part of the barrel its size must be moderate enough to allow the passage of the piston during the assembly of the syringe. Therefore, the bead cannot effectively prevent the piston from being pulled out of the barrel.

From DE patent application publication No. 2,329,390 it is known to weld or otherwise fix an inwardly protroding flange to the rear end of the barrel of a hypodermic syringe after the piston has been placed in the barrel. The flange prevents the piston from being pulled out of the barrel. During the welding process the flange and the barrel must be carefully positioned relative to each other. For barrels of different diameters different flanges have to be produced.

The purpose of the present invention is to provide a disposable syringe which eliminates the above-mentioned drawbacks connected with the disposable syringes according to the known art.

SUMMARY OF THE INVENTION

According to the present invention there is provided a disposable syringe which is characterized in that the barrel is provided with a small blob of a cured sealant or other adhesive substance, which, after the piston or piston and piston rod has been placed in the barrel, is applied in uncured form to the inner surface of the barrel at a position between the open rear end of the barrel and the piston in its rearmost position. The use of a small blob of a cured sealant or other adhesive substance to restrict the movement of the piston has several advantages. By the use of the syringe according to the invention the spillage and contamination which may occur with other disposable syringes is avoided. The sealant is cheap and it can be applied automatically on a packing line. In contradiction to a flange or the like to be mounted on a syringe in order to achieve a similar result the blob of sealant according to the present invention is universal to syringes of all sizes, except for a possible adjustment of the size of the blob of sealant. No investments in expensive tools for the manufacture of said flange are necessary.

The syringe barrel can be made of glass and the glass barrel can be coated with silicone. Alternatively the syringe barrel can be made of thermoplastic material, for example of polyethylene, polypropylene, PMP (poly-4-methylpenten-1) or a polyamide or any other suitable thermoplastic material.

The sealant or adhesive substance used for the blob can for example be a silicone sealant, a cyanoacylate based adhesive or an epoxy based adhesive, but other types of sealants or adhesives may also be used. The sealant or adhesive substance preferably is so viscous that it only runs insignificantly if at all when it is applied to the syringe barrel.

In some cases it will be possible to apply the sealant or the adhesive substance in such a precisely measured quantity and at a so well-defined position in the syringe barrel that the blob will not come in contact with the piston or the piston rod. Consequently, these will not adhere to the blob. However, if adhesion is a potential problem it can also be avoided by treating the piston and/or the piston rod with a repellant, for example an oil solution, or by mounting a sleeve made of paper, plastic foil or metal foil on the piston rod.

According to one preferred embodiment of the invention the syringe barrel is made of glass and coated with silicone prior to the application of the sealant and the sealant is a silicone sealant. The silicone sealant has a suitable viscosity and adheres well to the glass whereas it does not adhere to the piston and the piston rod when these are made of suitable materials or suitably treated materials. Coating with silicone is a usual measure taken with glass barrels for syringes to prevent the piston from sticking even after long storage and to make the piston move more smoothly in operation. Also in other connections silicone coating of glass and other materials serves as an anti-adhesion measure. Surprisingly, however, silicone coating of the syringe barrels made of glass does not adversely influence the adhesion of the silicone sealant to the glass.

According to another preferred embodiment of the invention the syringe barrel is made of glass which is not coated with silicone and the sealant or adhesive substance is a silicone sealant, a cyanoacrylate based adhesive substance or an epoxy based adhesive substance.

According to a further preferred embodiment of the invention the syringe barrel is made of a thermoplastic polyamide and the sealant or adhesive substance is a silicone sealant, a cyanoacrylate based adhesive substance or an epoxy based adhesive substance.

According to a further preferred embodiment of the invention the syringe barrel is made of PMP (poly-4-methylpenten-1) and the sealant or adhesive substance is a silicone sealant, a cyanoacrylate based adhesive substance or an epoxy based adhesive substance.

According to a further preferred embodiment of the invention the syringe barrel is made of polyethylene and the adhesive substance is a cyanoacrylate based adhesive.

According to a still further preferred embodiment of the invention the syringe barrel is made of polypropylene and the adhesive substance is a cyanoacrylate based adhesive.

BRIEF DESCRIPTION OF THE DRAWING

The drawing shows a sectional view along the longitudinal axis of a disposable hypodermic syringe according to the invention.

DETAILED DESCRIPTION OF A PREFERRED EMBODIMENT

A syringe barrel 4 which can be made of glass or a suitable thermoplastic material is equipped at the front end 3 with a hypodermic needle 2 and a cap 1 which protects the hypodermic needle. Alternatively the syringe barrel can be equipped with a gland for fixing a hypodermic needle, which gland may also be protected by a suitable cap. A piston 5 is displaced in the syringe barrel by means of a piston rod 9. A small blob 6 of cured sealant or adhesive substance secures the piston 5 against slipping out of the open rear end 8 of the syringe barrel 4. The exact amount of sealant or adhesive substance in the blob is not critical but will of course to some degree depend on the size of the syringe and especially on the diameter of the barrel and the piston. A guide to the amount of sealant or other adhesive substance will be found in Example 1.

The disposable hypodermic syringe according to the invention is especially useful when injections are to be performed by lay people, unexperienced in handling a hypodermic syringe. For example the syringe can form part of an emergency kit to be used for treating hypoglycemic diabetics. Hypoglycemia can be relieved by injection of glucagon, and the emergency kit can thus consist of a vial containing the required amount of lyophilized glucagon and a disposable syringe according to the invention containing the required amount of sterile water. In use the contents of the syringe is transferred to the vial and after complete dissolution of the glucagon the solution is drawn back into the syringe. If an ordinary disposable syringe were used for this operation there would be a risk that the piston would slip out of the barrel since the operation would typically be performed by an unexperienced and possibly nervous person. When in a syringe according to the invention the piston hits the blob of cured sealant or other adhesive substance it can go no further back and thus cannot slip out of the barrel.

The use of the disposable syringe according to the invention is not limited to the above emergency kit. Rather the disposable syringe according to the invention can be used for the same purposes as any ordinary disposable syringe.

Example 1 illustrates the production of disposable syringes according to the invention and containing 1 ml of sterile water.

EXAMPLE 1

Silicone coated glass barrels having an internal diameter of 8.5 mm and an internal length of 35 mm and having a fixed hypodermic needle were cleaned and equipped with a clean cap to protect the needle. The barrels were placed on a filling line with the rear end of the barrel pointing upwards. One ml of purified water was transferred to each barrel and a piston made of bromobutyl rubber was pushed down to the surface of the water. The ensemble was then autoclaved in order to obtain sterility. Finally a polypropylene piston rod with a threaded end was screwed into the piston and a blob of Silastic ® 732 RTV silicone sealant weighing about 250 mg (corresponding to a volume of about 240 $mm^3$ of sealant) was delivered from an automatic dispensing unit to the inner surface of the barrel at a position between the piston and the open rear end of the barrel (Silastic ® is a registered trade mark of Dow Corning Corporation). After curing, the sealant neither adhered to the piston nor to the piston rod whereas it adhered well to the glass barrel.

EXAMPLE 2

A blob of an epoxy based adhesive substance (about 300 mg, "Super Epoxy", obtained from Plastic Padding) was applied to the inner surface near the open rear end of the barrel of a complete disposable hypodermic syringe with a barrel made of PMP. The barrel had an internal diameter of 17 mm and an internal length of 65 mm. After curing the blob of adhesive substance adhered well to the wall of the barrel and the piston could not be pulled beyond the blob.

EXAMPLE 3

A blob of a cyanoacrylate based adhesive substance (about 300 mg, "Loctite 409", obtained from Loctite Corp.) was applied to the inner surface near the open rear end of the barrel of a complete disposable hypodermic syringe with a barrel made of polypropylene. The barrel had an internal diameter of 17 mm and an internal length of 65 mm. After curing the blob of adhesive substance adhered well to the wall of the barrel and the piston could not be pulled beyond the blob.

We claim:

1. In a disposable hypoderamic syringe of the type comprising a barrel having an inner surface and an open end, means for connecting a hypodermic needle to the barrel, a piston disposed in the barrel, and a piston rod secured to the piston and extending out of the open end of the barrel, the improvement comprising:

a quantity of a cured adhesive substance formed of a material dissimilar to that of the barrel and secured to the inner surface between the open end of the barrel and the piston, said quantity of cured adhesive substance sized to prevent the piston from moving past the quantity of cured adhesive substance, out of the open end of the barrel.

2. A disposable hypodermic syringe according to claim 1, characterized in that the syringe barrel is made of glass.

3. A disposable hypodermic syringe according to claim 1, characterized in that the syringe barrel is coated with silicone.

4. A disposable hypodermic syringe according to claim 1, characterized in that the syringe barrel is made of a thermoplastic material.

5. A disposable hypodermic syringe according to claim 4, characterized in that the syringe barrel is made up of a material selected from the group consisting of PMP (Poly-4-methylpenten-1) and polyamide.

6. A disposable hypodermic syringe according to claim 4, characterized in that the syringe barrel is made of a material selected from the group consisting of polyethylene and polypropylene.

7. A disposable hypodermic syringe according to claim 1 or 2 or 3 or 4 or 5 or 6, characterized in that the adhesive substance is a silicone sealant.

8. A disposable hypodermic syringe according to claim 2, 4, 5 or 6, characterized in that the adhesive substance is a cyanoacrylate based adhesive substance.

9. A disposable hypodermic syringe according to claim 2 or claim 5, characterized in that the adhesive substance is an epoxy based adhesive substance.

10. A method for assembling a disposable hypodermic syringe comprising the following steps:
 (a) providing a hypodermic syringe comprising a barrel having an inner surface and an open end, means for connecting a hypodermic needle to the barrel, a piston disposed in the barrel, and a piston rod secured to the piston and extending out of the open end of the barrel;
 (b) applying a quantity of an uncured adhesive to the inner surface of the barrel between the piston and the open end of the barrel; and
 (c) allowing the quantity of uncured adhesive to cure to form an obstruction sized to prevent the piston from moving past the obstruction, out of the open end of the barrel.

11. The method of claim 10 wherein the providing step comprises the step of providing the hypodermic syringe having a glass barrel.

12. The method of claim 10 further comprising the step of coating the inner surface with silicone prior to step (b).

13. The method of claim 10, wherein the providing step comprises the step of providing the hypodermic syringe having a thermoplastic barrel.

* * * * *

UNITED STATES PATENT AND TRADEMARK OFFICE
CERTIFICATE OF CORRECTION

PATENT NO. : 5,037,382

DATED : August 6, 1991

INVENTOR(S) : Ingelise Kvorning et al

It is certified that error appears in the above-identified patent and that said Letters Patent is hereby corrected as shown below:

On the title page, item [56], under the heading "FOREIGN PATENT DOCUMENTS," please insert --2329390 1/1974 W. Germany--.

In column 2, line 37, after "smoothly" please insert --when--.

Column 4,

In claim 1, line 1, please delete "hypoderamic" and substitute therefor --hypodermic--.

Signed and Sealed this

Nineteenth Day of January, 1993

Attest:

DOUGLAS B. COMER

*Attesting Officer*     *Acting Commissioner of Patents and Trademarks*